United States Patent [19]
Faries, Jr. et al.

[11] Patent Number: 5,857,467
[45] Date of Patent: Jan. 12, 1999

[54] REINFORCED SURGICAL DRAPES FOR USE WITH THERMAL TREATMENT SYSTEMS

[75] Inventors: Durward I. Faries, Jr., McLean, Va.; Bruce R. Heymann, Silver Spring, Md.

[73] Assignee: O.R. Solutions, Inc., Chantilly, Va.

[21] Appl. No.: 880,189

[22] Filed: Jun. 20, 1997

[51] Int. Cl.$^6$ .................................................. A61B 19/00
[52] U.S. Cl. .......................................... 128/849; 128/853
[58] Field of Search ..................................... 128/849–856

[56] References Cited

U.S. PATENT DOCUMENTS

| | | |
|---|---|---|
| 3,902,484 | 9/1975 | Winters . |
| 4,393,659 | 7/1983 | Keyes et al. . |
| 4,474,016 | 10/1984 | Winchell . |
| 4,522,041 | 6/1985 | Manzel . |
| 4,782,835 | 11/1988 | Bernardini . |
| 4,934,152 | 6/1990 | Templeton . |
| 5,040,699 | 8/1991 | Gangemi . |
| 5,042,455 | 8/1991 | Yue et al. . |
| 5,163,299 | 11/1992 | Faries, Jr. et al. . |
| 5,174,306 | 12/1992 | Marshall . |
| 5,310,524 | 5/1994 | Campbell et al. . |
| 5,331,820 | 7/1994 | Faries, Jr. et al. . |
| 5,333,326 | 8/1994 | Faries, Jr. et al. . |
| 5,363,746 | 11/1994 | Gordon . |
| 5,374,813 | 12/1994 | Shipp . |
| 5,383,476 | 1/1995 | Peimer et al. . |
| 5,386,835 | 2/1995 | Elphick et al. . |
| 5,400,267 | 3/1995 | Denen et al. . |
| 5,400,616 | 3/1995 | Faries, Jr. et al. . |
| 5,402,644 | 4/1995 | Faries, Jr. et al. . |
| 5,429,801 | 7/1995 | Faries, Jr. et al. . |
| 5,435,322 | 7/1995 | Marshall . |
| 5,443,082 | 8/1995 | Mewburn . |
| 5,449,892 | 9/1995 | Yamada . |
| 5,457,962 | 10/1995 | Faries, Jr. et al. . |
| 5,463,213 | 10/1995 | Honda . |
| 5,502,980 | 4/1996 | Faries, Jr. et al. . |
| 5,522,095 | 6/1996 | Faries, Jr. et al. . |
| 5,524,643 | 6/1996 | Faries, Jr. et al. . |
| 5,551,240 | 9/1996 | Faries, Jr. et al. . |
| 5,615,423 | 4/1997 | Faries, Jr. et al. . |
| 5,653,938 | 8/1997 | Faries, Jr. et al. . |

*Primary Examiner*—Michael A. Brown

[57] ABSTRACT

Reinforced surgical drapes are utilized in combination with a thermal treatment system including a basin recessed in a top surface of a system housing to ensure sterility of a sterile medium and to reduce drape costs. A reinforced surgical drape typically includes a primary drape layer of relatively thin construction that may puncture or tear under stress and at least one reinforcing layer selectively attached to drape portions receiving stress during use to prevent the drape from puncturing or tearing. Each reinforcing layer includes at least one segment that may either reinforce substantially the entire drape or the stressed drape portions. Alternatively, a surgical drape may be reinforced by disposing at least one drape over another drape placed on a thermal treatment system. The multiple drape embodiment enables immediate generation of a sterile field above a previously used or damaged drape, and further enables reuse of an underlying drape since an overlying drape provides the sterile field. The reinforced and multiple drapes may further be utilized in substantially the same manner described above in thermal treatment systems having single or multiple basins for warming, cooling and/or congealing the sterile medium.

34 Claims, 7 Drawing Sheets

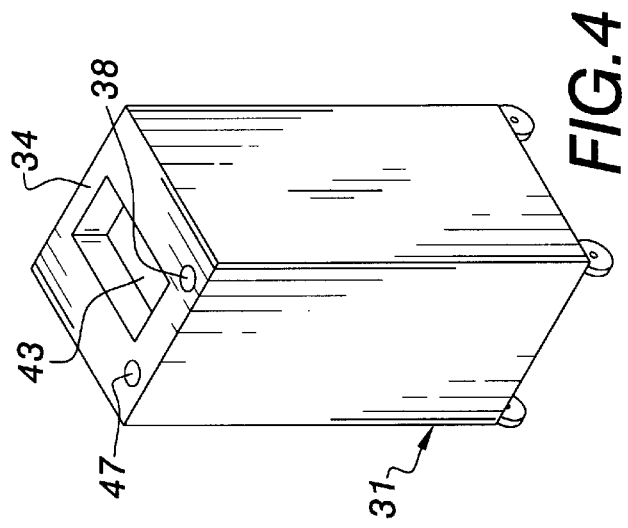
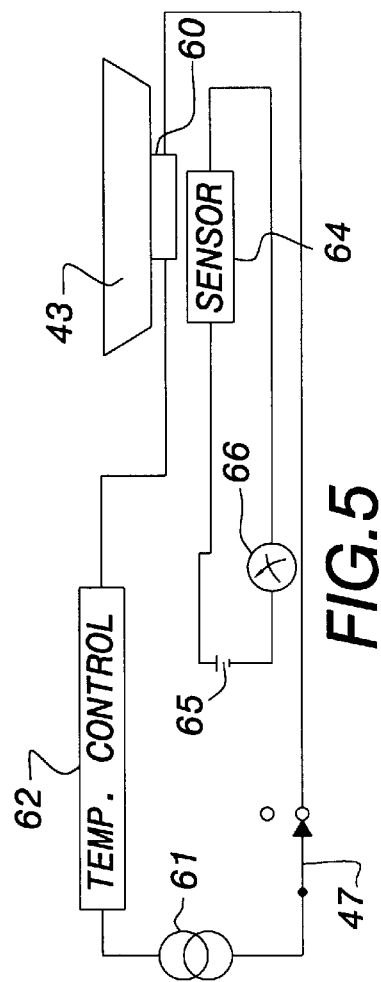

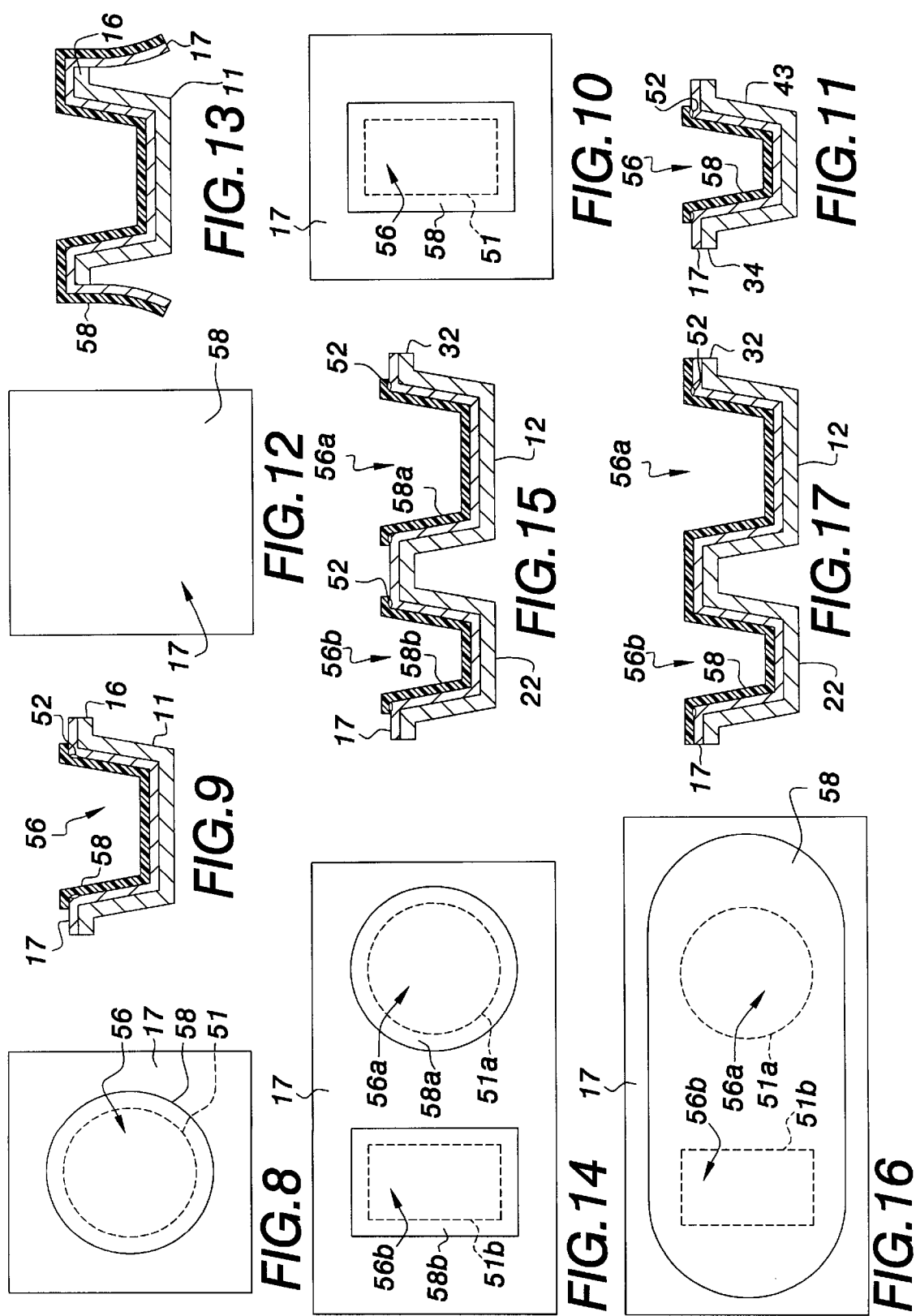

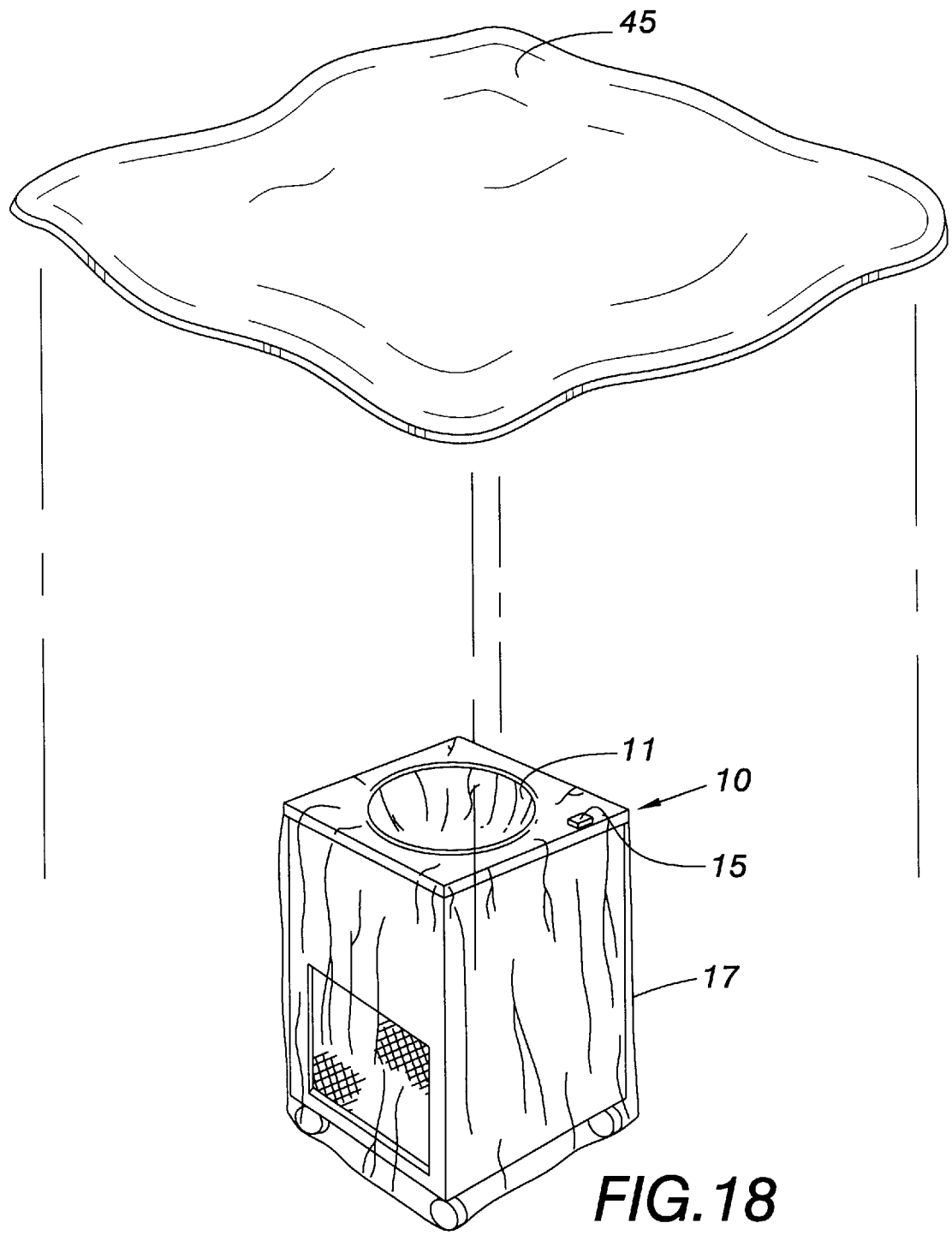

REINFORCED SURGICAL DRAPES FOR USE WITH THERMAL TREATMENT SYSTEMS

BACKGROUND OF THE INVENTION

1. Technical Field

The present invention pertains to improvements in methods and apparatus for heating or cooling sterile surgical liquids and collecting surgical sterile slush. In particular, the present invention is an improvement of the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al), 5,333,326 (Faries, Jr. et al), 5,457,962 (Faries, Jr. et al), 5,522,095 (Faries, Jr. et al), 5,524,643 (Faries, Jr. et al) and copending U.S. patent application Ser. Nos. 08/810,025, filed Mar. 4, 1997 and entitled "Surgical Drape For Use in Forming and Collecting Surgical Slush" and 08/810,104, filed Feb. 25, 1997 and entitled "Surgical Drape For Use With Surgical Slush Machines Having an Automatic Dislodgement Mechanism". The disclosures in those patents and copending applications are expressly incorporated herein by reference in their entireties.

2. Discussion of the Prior Art

The above-referenced Keyes et al patent (U.S. Pat. No. 4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent (U.S. Pat. No. 4,934,152), the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent (U.S. Pat. No. 4,934,152) discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al patent (U.S. Pat. No. 5,163,299) notes that scraping congealed liquid from the drape is undesirable in view of the potential for damage to the drape, resulting in a compromise of sterile conditions. As a solution to the problem, the Faries, Jr. et al patent (5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The Faries, Jr. et al patent (U.S. Pat. No. 5,331,820) resolves the problem of manual manipulation of the drape by providing several techniques to automatically remove the congealed liquid adhering to the drape without endangering the integrity of the drape. For example, one such technique includes providing a flat disk or plate at the bottom of the basin under the drape, wherein the plate is moved in an up and down manner to disengage the congealed liquid from the drape. The plate may be attached to a mechanism below the basin, or to the drape itself as disclosed in the Faries, Jr. et al patent (U.S. Pat. No. 5,457,962).

The Templeton patent (U.S. Pat. No. 4,934,152) further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, the Faries, Jr. et al patents (U.S. Pat. Nos. 5,333,326 and 5,522,095) disclose a manner in which to simultaneously provide both surgical slush and warmed surgical liquid during a surgical procedure by utilizing a machine having multiple basins with each basin either producing surgical slush or heating a sterile liquid. This machine typically utilizes a single surgical drape that forms a drape receptacle within each basin to collect sterile slush and heated sterile liquid produced by the machine in the respective basins.

The above-described apparatus may stand some improvement. In particular, sterile surgical drapes used with thermal treatment systems (e.g., systems that warm, cool or congeal sterile liquid) are made of a certain thickness to assure that areas of the drape that are stressed during use are not torn or punctured in order to maintain, and avoid compromising, the sterile field. Stress may be applied to the drape, for example, from forces exerted when placing and/or removing the drape from a thermal treatment system, manually or automatically manipulating the drape to dislodge congealed sterile medium as described above, and/or collecting the sterile liquid or slush within a drape container (i.e., forces exerted onto the drape by the weight of the sterile liquid or slush). Although thick drapes resist tearing and puncture, such thick drapes are relatively expensive to manufacture, and are also expensive to store and ship because they are bulky and heavy due to thicker material required for their construction. These thick drapes are also less malleable, thereby degrading drape handling for various aspects of a surgical procedure, such as installation of the drape on a thermal treatment system. By way of example, if sterile liquid impermeability and sterile field protection are the only considerations, the drape may be made of much thinner material, thereby being lighter, more malleable and less costly to manufacture. However, additional strength is required to prevent tearing or puncture of the drape from stress created by manipulation during slush formation, or even proper placement and removal in warming and cooling applications as described above. Thus, there exists a need in the art for drapes of relatively thin construction to reduce drape costs and enhance drape malleability and handling, while being of sufficient strength to withstand stress applied to the drape during normal use.

Further, it is desirable that the above-described apparatus provide a manner in which to reinforce surgical sterile drapes during a surgical procedure such that an immediate sterile field may be created above a previously used and/or damaged surgical drape disposed on a thermal treatment system. In particular, such a manner is needed when a surgical drape ruptures or is otherwise damaged during a surgical procedure. The damaged drape compromises sterility of the sterile liquid or slush and may contaminate the entire surgical procedure, thereby requiring an immediate replacement drape and sterile liquid to avoid risk of injury to a patient. Although the damaged drape and contaminated liquid or slush may be removed for disposal and replacement, this process requires additional time that may be crucial during a surgical procedure.

Moreover, several of the drapes disclosed in the above mentioned patents and copending applications include specialized features to enhance various aspects of thermal treatment system operation. For example, the above-mentioned Faries, Jr. et al patent (U.S. Pat. No. 5,457,962) discloses a surgical drape having a plate that engages a dislodgement mechanism disposed within a thermal treatment system basin wherein the plate in combination with the dislodgement mechanism manipulates the drape to dislodge congealed sterile medium adhered to the drape. However, since the plate substantially increases drape costs, it is desirable to determine a cost efficient manner to reuse these plate drapes to forego the expense of purchasing a new plate drape for each use of the thermal treatment system during surgical procedures. Similarly, drapes including other specialized features, such as the bladder drapes disclosed in copending application Ser. No. 08/810,025 and the sensor drapes disclosed in the Faries, Jr. et al patent (U.S. Pat. No. 5,524,643), tend to have relatively high costs, and it is desirable to determine cost efficient manners to reuse these specialized drapes to forego the expense of repurchasing these expensive drapes for each use of the thermal treatment system during surgical procedures.

In addition, some surgical drapes include specific enhancements to overcome anomalies when used with thermal treatment systems. For example, the above-mentioned copending application Ser. No. 08/810,104 is directed toward enhancing dislodgement of congealed sterile medium formed within a thermal treatment system basin having a dislodgement mechanism. The dislodgement mechanism typically includes a reciprocating plate to manipulate the drape and dislodge congealed sterile medium adhered to the drape. In particular, that copending application is directed toward preventing a drape disposed over the thermal treatment system and within the basin from being drawn beneath the dislodgement mechanism reciprocating plate. Since the dislodgement mechanism becomes ineffective (i.e., does not effectively manipulate a drape) once a drape is drawn beneath the reciprocating plate, the copending application discloses several techniques for preventing the drape from being drawn beneath the reciprocating plate. One such technique includes constructing surgical drapes of materials having a coefficient of friction in a particular range such that a drape may adhere to the basin walls and withstand being drawn under the reciprocating plate. A further technique disclosed in the copending Ser. No. 08/810,104 application proposes attaching securing and other devices to the drape to secure the drape to the thermal treatment system and prevent the drape from being drawn beneath the reciprocating plate. However, it is desirable to alleviate the above described and other surgical drape anomalies without substantially modifying or providing additional components for the drape that increase drape costs.

OBJECTS AND SUMMARY OF THE INVENTION

Accordingly, it is an object of the present invention to reduce drape and overall thermal treatment system costs by utilizing surgical drapes of thinner construction in conjunction with thermal treatment systems to contain sterile liquid or slush within thermal treatment system basins.

It is another object of the present invention to selectively strengthen or reinforce a thin sterile drape to provide an inexpensive yet durable drape container in a thermal treatment system basin, while enhancing drape malleability and handling for various aspects of thermal treatment system operation, such as installation of the drape on the thermal treatment system.

Yet another object of the present invention is to reinforce sterile drapes by selectively bonding multiple layers of material over the entire drape or particular drape portions subjected to stress during normal use.

Still another object of the present invention to reinforce surgical drapes in a manner that quickly provides a sterile field above a previously used and/or damaged drape disposed over a thermal treatment system.

A further object of the present invention is to reduce drape and overall thermal treatment system costs by enabling reuse of expensive specialized drapes (e.g., drapes including dislodgement mechanism plates, bladders for dislodging congealed sterile medium, sensors for detecting the presence of a leak, etc.) on thermal treatment systems, while maintaining a sterile field above the reused drape.

The aforesaid objects are achieved individually and in combination, and it is not intended that the present invention be construed as requiring two or more of the objects to be combined unless expressly required by the claims attached hereto.

According to the present invention, a sterile drape used as a container within a thermal treatment system basin for collecting sterile liquid or slush is made of a thin material sufficient to provide the required sterile field and impermeability for sterile liquid to be contained, but of insufficient thickness to totally eliminate the likelihood of rupturing, tearing, puncturing or other damage during normal use. In order to preclude such drape damage, substantially the entire drape or selected portions of the drape are reinforced preferably with an additional drape layer or multiple (i.e., at least two) drape layers of the same or similar material and thickness as the primary or base layer of the drape. Each additional drape layer preferably includes at least one layer segment wherein each layer segment typically has dimensions substantially similar to or less than the dimensions of the drape in order to respectively reinforce substantially the entire drape or corresponding selected portions of the drape (i.e., a layer segment may be of varying size in order to reinforce substantially the entire drape or reinforce only selected portions of the drape). The selected portions of the drape are those portions that are typically subjected to stress during installation or use. The drape layers are bonded together by heat sealing, ultrasonic welding, or the like, at least along the periphery of the smaller of the two (or more)

layers or along the peripheries of the joined layers if plural full size drapes are used. The resulting drape unit has sufficient strength to perform its intended functions without compromising the sterile field, but is significantly less expensive than conventional drapes used for these functions. Additional advantages of this drape include the relative ease with which it can be handled during installation and its reduced weight and bulk during transportation. The reinforced drape may be utilized with single or multiple basin thermal treatment systems of the type that warm, cool and/or congeal a sterile medium (e.g., liquid). In addition, the reinforced drapes may be utilized with thermal treatment systems of the type that include dislodgement mechanisms within their basins for dislodging congealed sterile medium adhered to the drape.

A sterile drape may alternatively be reinforced by placing additional sterile drapes over an original sterile drape when the original sterile drape is disposed on a thermal treatment system. Specifically, a sterile drape is disposed over a top surface of a thermal treatment system having a basin recessed in the top surface for containing a sterile medium (e.g., liquid). A portion of the drape is pushed down into and conforms to the basin to form a drape container or receptacle within the basin for collecting the sterile medium. The thermal treatment system may be of the type that either congeals or warms the sterile medium to respectively produce sterile slush or a warm sterile liquid within the basin. Thermal treatment systems that congeal the sterile medium may further include a dislodgement mechanism typically of the type having a reciprocating plate. The plate reciprocated by the dislodgement mechanism may be part of or integral with that mechanism, or may be attached to a sterile drape for engagement with the dislodgement mechanism as disclosed in the respective Faries, Jr. et al patents (U.S. Pat. No. 5,331,820 and U.S. Pat. No. 5,457,962). The reciprocating plate, via the dislodgement mechanism, manipulates the drape to dislodge congealed sterile medium adhering to the drape in substantially the same manner disclosed in the respective Faries, Jr. et al patents (U.S. Pat. No. 5,331,820 and U.S. Pat. No. 5,457,962). An additional reinforcing sterile drape is disposed on the thermal treatment system over the original drape in substantially the same manner described above for the original drape to contain the sterile medium and quickly provide a sterile field above the original drape in case of damage or rupture during a surgical procedure. Further, the reinforcing drape may enable the original drape, preferably including expensive specialized features (e.g., the reciprocating plate), to be reused as described below. Moreover, the additional reinforcing sterile drape may enhance thermal treatment system operation, such as dislodgement of congealed sterile medium, as described below.

The utilization of multiple drapes provides for immediate generation of a sterile field above a previously used and/or damaged (i.e., typically non-sterile) drape without having to dispose of the original drape during a surgical procedure. Further, since each drape forms a drape receptacle within the basin, the additional drape reinforces the original drape such that drapes of thinner construction may be utilized to reduce drape and thermal treatment system costs without fear of damage to the drape or contamination of the sterile medium. Moreover, an original drape containing a dislodgement mechanism plate and typically having relatively high costs may be reused to engage the dislodgement mechanism, while more economical or inexpensive drapes may be placed over the underlying (i.e., typically non-sterile) plate drape to provide the sterile field. Similarly, drapes including other specialized features (e.g., bladders for dislodging congealed sterile medium, sensors for detecting the presence of a leak, etc.) may be reused, while more economical or inexpensive drapes provide the sterile field above the underlying (i.e., typically non-sterile) specialized drape. For example, the sensor drape disclosed in the Faries, Jr. et al patent (U.S. Pat. No. 5,524,643) includes electronic sensors that detect the presence of solution in a basin. These sensors dramatically increase drape costs. However, a more economical or inexpensive drape (e.g., a basic non-fitted surgical sterile drape) disposed over the sensor drape enables the sensor drape to be reused, wherein the economical drape provides a sterile field, while the reused sensor drape detects leaks within the economical drape by detecting the presence of sterile medium escaping the economical drape and residing between the drapes. Thus, the inexpensive drapes are required to be purchased for each use of the thermal treatment system to provide the sterile field, while the more expensive specialized drapes are purchased less frequently, thereby reducing overall thermal treatment system costs.

The additional reinforcing drape may be disposed over the original underlying drape after placement of the original drape on the thermal treatment system (i.e., this is preferable for the thinner drapes), or after use of that original drape for a surgical procedure. Further, subsequent reinforcing drapes may be disposed over previously used reinforcing drapes to provide a sterile field above those previously used reinforcing drapes in substantially the same manner described above. The additional reinforcing drapes may be utilized in substantially the same manner described above for thermal treatment systems having a plurality of basins for heating and/or cooling a sterile medium wherein the reinforcing drape may be an economical or inexpensive drape to provide the sterile field, while the original drape may be a more expensive specialized drape (e.g., include plates and/or other components or modifications as described above).

Moreover, the additional reinforcing drapes may be utilized in combination with various other drape and thermal treatment system embodiments to enhance thermal treatment system operation. For example, the reinforcing drapes may be utilized to enhance operation of thermal treatment systems having automatic dislodgement mechanisms for dislodging congealed sterile medium adhered to surgical drapes. These dislodgement mechanisms, such as the mechanisms disclosed in the above-mentioned Faries, Jr. et al patents (U.S. Pat. No 5,331,820 and U.S. Pat. No. 5,457,962), include a reciprocating plate that tends to draw portions of surgical drapes beneath the reciprocating plate, thereby inhibiting manipulation of the drape and dislodgement of congealed sterile medium. The utilization of reinforcing drapes with these types of dislodgement mechanisms ensures that only portions of the original underlying drape are drawn beneath the reciprocating plate, thereby enabling the dislodgment mechanism to manipulate the additional reinforcing drape and dislodge congealed sterile medium.

The above and still further objects, features and advantages of the present invention will be apparent upon consideration of the following detailed description of the specific embodiments thereof, particularly when taken in conjunction with the accompanying drawings wherein like reference numerals in the various figures are utilized to designate like components.

BRIEF DESCRIPTION OF THE DRAWINGS

FIG. 4 is a view in perspective of a thermal treatment system of the type employed by the present invention for warming a sterile medium.

FIG. 5 is an electrical schematic diagram of a heating unit employed in the thermal treatment system of FIG. 4.

FIG. 8 is a top view in plan of a surgical drape having a selectively reinforced portion corresponding to a thermal treatment system basin congealing a sterile medium according to an embodiment of the present invention.

FIG. 9 is a view in elevation and section of the drape of FIG. 8 disposed in a thermal treatment system basin congealing a sterile medium.

FIG. 10 is a top view in plan of a surgical drape having a selectively reinforced portion corresponding to a thermal treatment system basin warming a sterile medium according to the present invention.

FIG. 11 is a view in elevation and section of the drape of FIG. 10 disposed in a thermal treatment system basin warming a sterile medium.

FIG. 12 is a top view in plan of a surgical drape having a reinforced portion encompassing substantially the entire drape according to another embodiment of the present invention.

FIG. 13 is a view in elevation and section of the drape of FIG. 12 disposed in a thermal treatment system basin congealing a sterile medium.

FIG. 14 is a top view in plan of a surgical drape for a multiple basin thermal treatment system having individual reinforced portions corresponding to thermal treatment system basins according to yet another embodiment of the present invention.

FIG. 15 is a view in elevation and section of the drape of FIG. 14 disposed in basins of a multiple basin thermal treatment system.

FIG. 16 is a top view in plan of a surgical drape for a multiple basin thermal treatment system having a selectively reinforced portion corresponding to multiple thermal treatment system basins according to still another embodiment of the present invention.

FIG. 17 is a view in elevation and section of the drape of FIG. 16 disposed in basins of a multiple basin thermal treatment system.

FIG. 18 is an exploded view in perspective of an additional reinforcing drape disposed over an underlying drape placed on a thermal treatment system according to a further embodiment of the present invention.

DETAILED DESCRIPTION OF THE PREFERRED EMBODIMENTS

Figure 1:
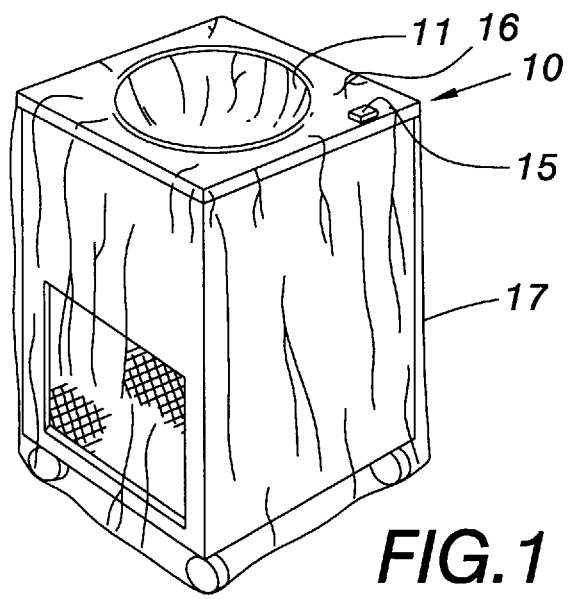
FIG. 1 is a view in perspective of a thermal treatment system and corresponding surgical drape of the type employed by the present invention for generating and collecting surgical slush.
Figure 2:
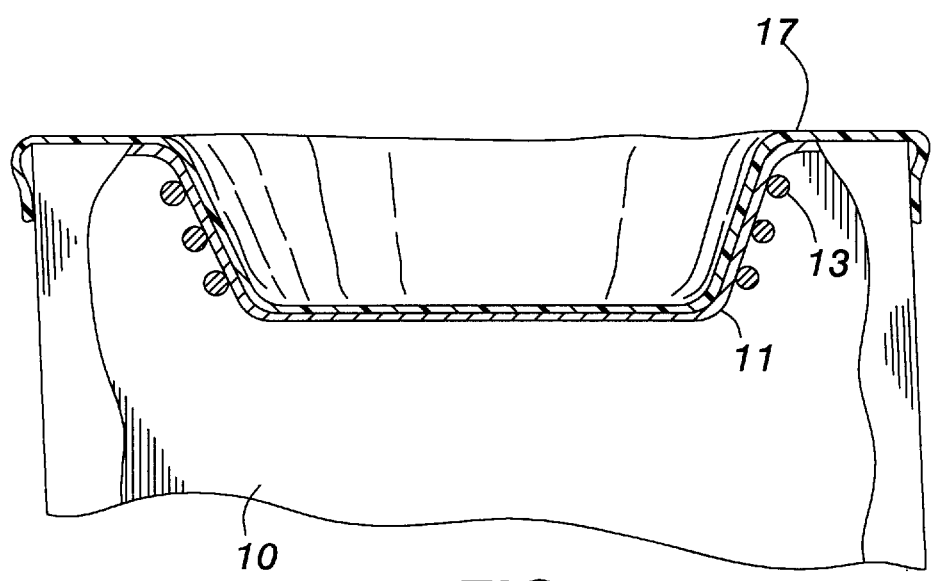
FIG. 2 is a view in elevation and partial section of the thermal treatment system and surgical drape of FIG. 1.

Referring to FIGS. 1–2 of the accompanying drawings, a thermal treatment machine or system for generating surgical slush of the type described in the above-referenced Templeton patent includes a cabinet or housing 10 with a top surface 16 having a basin 11 mounted thereon in an appropriately sized recess. Basin 11 may be of any shape, however, by way of example only, the basin is substantially circular. Basin 11 is made of thermally conductive material, typically stainless steel, and includes a generally flat bottom wall and frusto-conical side wall. A conventional refrigeration unit is disposed within cabinet 10 and typically includes a compressor, a condenser and an expansion control unit connected by appropriate fluid conduits in a closed refrigeration loop of evaporator 13. The evaporator is in the form of a coil wound about the exterior surface of basin 11 in thermal transfer relation therewith. The refrigeration unit is activated via appropriate controls 15, while evaporator 13 cools the side wall of basin 11 to a temperature substantially below the freezing temperature of the liquid used in forming the sterile slush. This temperature is preferably on the order of −32° F. to 10° F. For further details of the structure and operation of the refrigeration unit, reference is made to the aforementioned Keyes et al and Templeton et al patents.

A sterile drape 17, preferably transparent, is typically disposed over the top and sides of cabinet 10 and made to conform to the side wall and bottom of basin 11. Controls 15 are disposed on top surface 16 of system cabinet 10 and are adjustable manually through drape 17. The portion of drape 17 disposed in basin 11 serves as a sterile receptacle for sterile liquid placed therein to be frozen into the desired sterile slush. Typical sterile liquid used to produce a surgical sterile slush is a 0.80% to 0.95% sodium chloride solution (i.e., saline). Drape 17 is made from a material that is impervious to the sterile liquid and sufficiently soft and flexible to conform to the basin walls. The drape may be non-fitted or flat (i.e., a plain or basic drape of sufficient length that is placed over the thermal treatment system), or be constructed such that the drape is formed to the contour of the cabinet housing for a more precise fit (i.e., a fitted drape). The thickness of the drape is preferably minimized to render thermal transfer therethrough most efficient, yet the thickness is sufficient to resist tearing and puncturing during normal use. Typically, drape 17 is made of materials commonly used in hospitals for surgical drapes and generally has a thickness in the approximate range of three through ten mils, however, drapes according to the present invention may be of thinner construction having thicknesses in the approximate range of one through three mils as described below. Drape 17 may also be made of polyurethane film as disclosed for the drape in the aforementioned Templeton patent, and may further include a preformed container portion (not shown) contoured to match the contour of a basin. The drape is designed to be disposable after a single use (i.e., a surgical procedure) and is provided presterilized and prepackaged in a manner to preserve its sterile state during storage.

Figure 3:
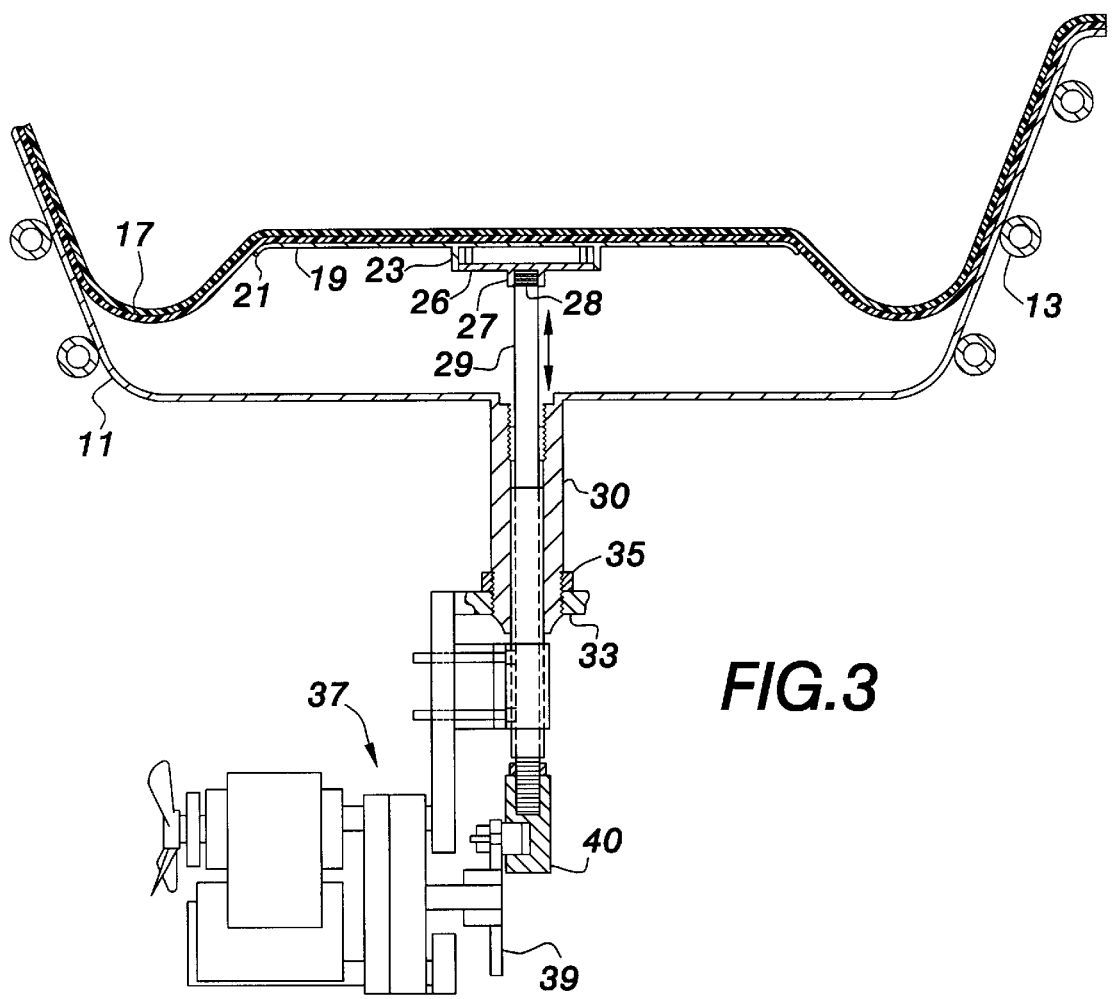
FIG. 3 is a view in elevation and partial section of a surgical drape disposed within a thermal treatment system basin having a dislodgement mechanism of the type employed by the present invention for manipulating the drape to dislodge congealed sterile medium adhered to the drape.

A thermal treatment system for generating surgical slush including a dislodgement mechanism of the type described in the above-mentioned Faries, Jr. et al patent (U.S. Pat. No. 5,457,962) and employed by the present invention to automatically manipulate drape 17 and dislodge congealed sterile medium is illustrated in FIG. 3. The thermal treatment system is substantially similar to the thermal treatment system described above for FIG. 1 except that the system of FIG. 3 includes a dislodgement mechanism to dislodge congealed sterile medium. Specifically, a disk or plate 19 may be bonded or attached to the drape at the underside of the receptacle portion and is configured to generally match the basin bottom while being supported, in a manner described below, slightly above the basin bottom between the drape and the basin. Plate 19 is generally circular with a short downturned annular lip 21 disposed at its circumference. Downturned annular lip 21 is rounded to avoid sharp edges that might inadvertently tear drape 17 during movement of the drape. Plate 19 is permanently bonded or attached to drape 17 (e.g., via a suitable adhesive) in flush abutment along the entire upper surface of the plate. Depending centrally from the bottom surface of plate 19 is an outer annular wall 23 having a short annular lip extending radially inward from the wall bottom edge. An axially shorter annular wall is spaced concentrically inward from wall 23 and likewise depends from the bottom surface of plate 19. Wall 23 is sufficiently resilient to permit a circular connector plate 26 to be received with a snap-fit engagement in the space bounded by wall 23. More particularly, connector plate 26 has a diameter slightly smaller than the diameter of the inside surface of annular wall 23 but slightly larger than the diameter of the annular inner edge of the short annular lip. Accordingly, when plate 19 is properly centered in basin 11 and pushed axially downward onto connector plate 26, the connector plate resiliently forces the short annular lip upward and wall 23 outward until the connector plate axially passes the short annular lip and its flat upper surface is stopped by the bottom annular edge of the inner annular wall. Once connector plate 26 clears the short annular lip, the short annular lip and wall 23 resiliently return to their unstressed position with the short annular lip extending a short radial distance along the bottom surface of the connector plate. Connector plate 26 is thusly engaged in a snap-fit by plate 19.

The bottom of connector plate 26 is provided with a centrally located downwardly depending hollow cylindrical stem 27. Stem 27 is interiorly threaded to receive a threaded tip 28 of a shaft 29 extending upwardly through the bottom of basin 11. In particular, the bottom of basin 11 is provided with a central hole communicating with a bore in an adapter tube 30 secured at its upper end to the bottom of basin 11 by any convenient mechanism. The bottom end of adapter tube 30 is externally threaded and is engaged by a support bracket 33 and lock washer 35 such that bracket 33 is suspended interiorly of the machine cabinet (not shown in FIG. 3). A gear motor assembly, generally designated at 37, is supported by bracket 33 and includes a rotor 39 operatively engaged with a bearing track 40. Drive shaft 29 has its bottom end operatively engaged to bearing track 40 to cause the shaft to reciprocate longitudinally as rotor 39 rotates. Shaft 29 extends upwardly through adapter tube 30 and has its upper end secured to the center of the underside of plate 26 in the manner described above. Accordingly, as motor 37 reciprocates shaft 29 up and down, the shaft moves plate 19 up and down. Plate 19, in turn, moves the bottom of the drape container up and down to loosen pieces of frozen saline that form on the drape. The loosened pieces fall and collect in the center of the drape container as surgical slush. For further details on operation of the dislodgement mechanism, reference is made to the aforementioned Faries, Jr. et al patent (U.S. Pat. No. 5,457,962).

A typical thermal treatment system for heating a sterile medium (i.e., liquid) of the type described in the above-mentioned Faries, Jr. et al (U.S. Pat. No. 5,333,326) patent and employed by the present invention is illustrated in FIG. 4. Specifically, the system includes a cabinet or housing 31 and a warming basin 43 recessed into a top surface 34 of cabinet 31. Basin 43 may be of any shape, however, by way of example only, the basin is substantially rectangular. A heater power switch 47 and a temperature controller/indicator 38 are provided on top surface 34 adjacent the warming basin. A surgical drape (not shown), substantially similar to the drape described above for FIG. 1, is typically disposed over the system to contain a sterile medium within basin 43 in substantially the same manner described above for the thermal treatment system of FIG. 1. The sterile medium is substantially the same medium described above to produce sterile slush wherein the sterile medium is warmed within the basin to produce a warmed sterile medium. It is to be understood that the thermal treatment systems described above may have various configurations (e.g., varying basin shapes) and include a plurality of basins warming and/or cooling a sterile medium as described below.

The manner of heating sterile liquid in warming basin 43 is illustrated schematically in FIG. 5. Specifically, an electrical circuit includes a power source 61 connected in series with a temperature control unit 62, a heater element or pad 60, and power control switch 47. Heater 60 is typically a thin wafer-like member disposed along the bottom surface of heating basin 43, secured to the basin by a suitable pressure sensitive adhesive having efficient heat transfer characteristics. Heater 60 has smaller dimensions than the basin bottom and is disposed at the approximate center of the bottom surface of the basin. The heater, for example, may be of the type described in the aforementioned Templeton patent. Temperature control unit 62 includes a device for adjusting current passing through the heating element 60 so as to permit selective adjustment of the heat applied to the liquid in basin 43. The power switch 47 permits selective application and removal of current flow with respect to heater 60.

A temperature sensor 64 is disposed adjacent basin 43 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicator 38 described above. For further details on the operation of the heating unit, reference is made to the Faries, Jr. et al (U.S. Pat. No. 5,333,326) and other abovementioned patents.

Figure 6:
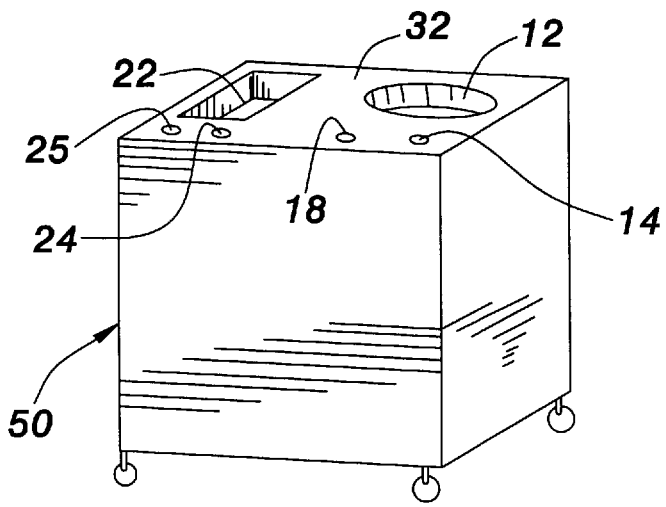
FIG. 6 is a view in perspective of a multiple basin thermal treatment system of the type employed by the present invention for heating and/or cooling a sterile medium.
Figure 7:
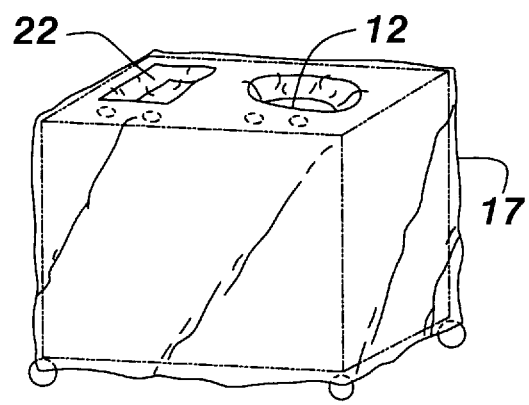
FIG. 7 is a view in perspective of a surgical drape positioned over the thermal treatment system of FIG. 6.

In addition, a multiple basin thermal treatment system of the type described in the above-mentioned Faries, Jr. et al patents (U.S. Pat. No. 5,333,326 and U.S. Pat. No. 5,522,095) and employed by the present invention is illustrated in FIGS. 6–7. Initially, an exemplary thermal treatment system having multiple basins for simultaneously cooling and heating sterile liquid has an integral assembly 50 including a slush basin 12 for slush phase medium and a warming basin 22 for heated liquid phase medium recessed into top surface 32 of a common cabinet. Also disposed in top surface 32 are a cooling unit power switch 18, a cooling unit temperature controller/indicator 14, a heater power switch 25 and a heater unit temperature controller/indicator 24. A drape 17 for use with the plural basin system is substantially similar to the drapes described above, but is of sufficient size to encompass the plurality of basins. For further details of the structure and operation of assembly 50, reference is made to the aforementioned Faries, Jr. et al patents (U.S. Pat. No. 5,333,326 and U.S. Pat. No. 5,522,095).

A reinforced drape for use with thermal treatment systems congealing a sterile medium of the type described above for FIG. 1 is illustrated in FIGS. 8–9. Specifically, drape 17 is substantially similar to the surgical sterile drapes described above except that the drape is of thinner construction, typically unable to withstand tearing or puncturing stress during normal use, and includes a reinforcing layer having a reinforcing layer segment 58 that provides additional thickness to a drape portion experiencing stress to prevent tearing or puncturing of the drape. The reinforcing layer typically includes at least one reinforcing layer segment wherein each reinforcing layer segment has dimensions substantially similar to or less than the drape in order to reinforce substantially the entire drape or corresponding selected portions of the drape as described below. The thickness of drape 17 is generally minimized to enhance drape malleability, simplify handling and reduce drape weight and cost. Typically, and by way of example only, drape 17 may have a thickness in the range of one through three mils, wherein each reinforcing layer segment selectively provides additional thickness to a corresponding drape portion that enables the drape to withstand stress. Drape 17 typically includes a basin portion 56 that corresponds to and is for disposal within a thermal treatment system basin 11 to serve as a sterile receptacle for sterile liquid. Basin portion 56 is defined by a basin perimeter 51 (i.e., shown in phantom on the drape illustrated in FIG. 8) indicating the portion of the drape to be disposed in basin 11, and may be of any shape to accommodate varying shaped thermal treatment system basins. By way of example only, basin portion 56 is substantially circular and accommodates thermal treatment systems having substantially circular basins for congealing a sterile liquid to a desired slush consistency as described above. Reinforcing or secondary layer segment 58 is bonded or attached to drape 17 or, in other words, the primary drape layer, coincident basin portion 56 to reinforce the basin portion by providing additional thickness to resist tearing and/or puncture stress applied to the drape basin portion during normal use. Reinforcing layer segment 58 may be of substantially the same material and thickness as the drape primary layer to reduce costs and enhance bonding, however, the reinforcing layer segment may include any suitable thickness or material. Reinforcing layer segment 58 may be of any shape, but is typically substantially circular to accommodate basin portion 56 and includes dimensions slightly larger than the basin portion such that when the drape is disposed on the thermal treatment system, the reinforcing layer segment extends beyond the basin periphery partially onto the drape portion residing on cabinet top surface 16. Reinforcing layer segment 58 is bonded to the sterile surface of drape 17, however, the reinforcing layer segment may be bonded to either the sterile or non-sterile surface of the drape. The reinforcing layer segment edges are typically bonded to the drape proximate basin perimeter 51 via a material weld or seam 52, or by use of adhesives, heat welding or any other conventional fastening techniques. Alternatively, substantially the entire area of reinforcing layer segment 58 may be bonded to the drape forming a double laminate drape. In addition, a single reinforcing layer segment or several reinforcing layer segments may be bonded to drape 17 coincident any drape portions receiving stress during normal use, or each reinforcing layer segment may be disposed integral with a corresponding primary drape layer portion to reinforce these portions and prevent tearing or puncturing of the drape in substantially the same manner described above. Additional reinforcing layers may be utilized on the drape wherein segments of the additional reinforcing layers are attached to the drape coincident existing reinforcing layer segments to further reinforce stressed drape portions in substantially the same manner described above.

A reinforced drape for use with thermal treatment systems warming a sterile medium of the type described above for FIG. 4 is illustrated in FIGS. 10–11. Specifically, drape 17 is substantially similar to the reinforced drape described above for the thermal treatment system congealing a sterile medium except that drape portion 56, defined by a basin perimeter 51 (i.e., shown in phantom on the drape illustrated in FIG. 10), is substantially rectangular to accommodate a substantially rectangular thermal treatment system warming basin 43. Basin portion 56 may alternatively be of any shape to accommodate varying shaped thermal treatment system basins as described above. A reinforcing layer segment 58 is bonded or attached to the sterile surface of drape 17 coincident basin portion 56, however, the reinforcing layer segment may be bonded to either the sterile or non-sterile surface of the drape via material welds 52 or other fastening techniques in substantially the same manner described above. Reinforcing layer segment 58 may be of any shape, but is typically substantially rectangular to accommodate basin portion 56 and includes dimensions slightly larger than the basin portion such that when the drape is disposed on the thermal treatment system, the reinforcing layer segment extends beyond the basin periphery partially onto the drape portion residing on cabinet top surface 16. The reinforcing layer segment reinforces basin portion 56 in substantially the same manner described above to resist stress applied to the drape during normal use that may cause the drape to tear and/or puncture. Further, a single reinforcing layer segment or several reinforcing layer segments may be bonded to drape 17 coincident any drape portions receiving stress during normal use, or each reinforcing layer segment may be disposed integral with a corresponding primary drape layer portion to prevent tearing or puncturing of the drape as described above. Moreover, additional reinforcing layers may be utilized to further reinforce the drape in substantially the same manner described above.

Alternatively, reinforcing layer segment 58 may be bonded or attached to drape 17 such that the reinforcing layer segment reinforces and is bonded coincident substantially the entire drape as illustrated in FIGS. 12–13. Specifically, drape 17 is substantially similar to the drapes described above for the thermal treatment systems congealing and warming a sterile medium except that reinforcing layer segment 58 includes dimensions substantially similar to drape 17 or, in other words, the primary drape layer. Reinforcing layer segment 58 is typically bonded to the sterile surface of drape 17, however, the reinforcing layer segment may be bonded to either the sterile or non-sterile surface of the drape. The reinforcing layer segment edges may be bonded to the drape via material welds 52, or reinforcing layer segment 58 may have substantially its entire area bonded to drape 17 forming a double laminate drape as described above. The thickness of the primary drape layer and reinforcing layer segment 58 are typically similar with each having a thickness less than the thickness of a single layer drape described above. This drape arrangement reduces drape costs since construction of reinforced drapes having two thin layers is substantially less than the cost of a single thicker layer drape. Further, several reinforcing layers each having segments including dimensions substantially similar to the drape may be bonded to substantially the entire drape in substantially the same manner described above. Moreover, a plurality of reinforcing layers may be utilized wherein each reinforcing layer may include segments having dimensions substantially similar to or less than the drape to respectively reinforce substantially the entire drape or corresponding selected portions of the drape (e.g., a reinforcing layer may reinforce a portion of the drape, while a subsequent reinforcing layer may reinforce substantially the entire drape). Drape 17 may be utilized on a thermal treatment system congealing or warming a sterile medium in substantially the same manner described above by pushing a portion of the drape down into a thermal treatment system basin to form a drape receptacle for containing the sterile medium.

A reinforced drape for use with a multiple basin thermal treatment system of the type described above for FIG. 6 is illustrated in FIGS. 14–15. Drape 17 is substantially similar to the reinforced drapes described above except that drape 17 is of sufficient size to accommodate multiple basins and is selectively reinforced by individual reinforcing layer segments 58*a*, 58*b* disposed coincident individual drape portions for disposal within basins of the multiple basin thermal treatment system as described below. Specifically, drape 17 includes basin portions 56*a*, 56*b* corresponding to and for disposal within basins 12, 22, respectively, of a multiple basin thermal treatment system, such as a thermal treatment system of the type described above for FIG. 6. Basin portion 56*a* is defined by a basin perimeter 51*a* (i.e., shown in phantom on the drape illustrated in FIG. 14) indicating the portion of the drape to be disposed within basin 12 wherein basin portion 56*a* is substantially circular to accommodate substantially circular basin 12 congealing a sterile medium as described above. Similarly, basin portion 56*b* is defined by a basin perimeter 51*b* (i.e., shown in phantom on the drape illustrated in FIG. 14) indicating the portion of the drape to be disposed in basin 22 wherein basin portion 56*b* is substantially rectangular to accommodate substantially rectangular basin 22 warming a sterile medium as described above. However, the basin portions 56*a*, 56*b* may be of any shape to accommodate varying shaped thermal treatment system basins. Individual reinforcing layer segments 58*a*, 58*b* are respectively bonded or attached to drape 17 coincident basin portions 56*a*, 56*b* to reinforce drape 17 by providing additional thickness to resist tearing and/or puncturing stresses applied to the basin portions during normal use as described above. Reinforcing layer segment 58*a* may be of any shape, but is substantially circular to accommodate basin portion 56*a*. Reinforcing layer segment 58*a* typically includes dimensions slightly larger than basin portion 56*a* such that when the drape is disposed on the thermal treatment system, reinforcing layer segment 58*a* extends beyond the periphery of basin 12 partially onto the drape portion adjacent basin 12 covering cabinet top surface 32. In a similar manner, reinforcing layer segment 58*b* may be of any shape, but is substantially rectangular to accommodate basin portion 56*b*. Reinforcing layer segment 58*b* typically includes dimensions slightly larger than basin portion 56*b* such that when the drape is disposed on the thermal treatment system, reinforcing layer segment 58*b* extends beyond the periphery of basin 22 and partially onto the drape portion adjacent basin 22 covering top surface 32. Reinforcing layer segments 58*a*, 58*b* are each typically bonded to the sterile surface of drape 17, however, the reinforcing layers may be bonded to either the sterile or non-sterile surface of the drape. The edges of the respective reinforcing layer segments may be bonded to the drape via material welds 52, or substantially the entire area of each layer segment 58*a*, 58*b* may be bonded to the drape to form a double laminate drape as described above. The primary drape layer or, in other words, drape 17 may be of thinner construction as described above such that the cost of the drape is significantly reduced by selectively reinforcing stressed drape portions. In addition, a single reinforcing layer segment or several reinforcing layer segments may be bonded to the drape coincident any drape portions receiving stress during use, or each reinforcing layer segment may be disposed integral with a corresponding primary drape layer portion to reinforce these drape portions and prevent tearing or puncturing of the drape in substantially the same manner described above. Additional reinforcing layers may be utilized on the drape wherein segments of the additional reinforcing layers are attached to the drape coincident existing reinforcing layer segments to further reinforce stressed drape portions in substantially the same manner described above. An alternative manner in which to reinforce drape 17 for multiple basin thermal treatment systems of the type described above for FIG. 6 is illustrated in FIGS. 16–17. Drape 17 is substantially similar to the drape described above for the multiple basin thermal treatment system except that drape 17 includes a single large reinforcement layer segment 58 bonded or attached to drape 17 that encompasses the portions of drape 17 disposed in thermal treatment system basins 12, 22. Specifically, drape 17 includes a substantially circular basin portion 56*a* defined by a basin perimeter 51*a* (i.e., shown in phantom on the drape illustrated in FIG. 16) and a substantially rectangular basin portion 56*b* defined by a basin perimeter 51*b* (i.e., shown in phantom on the drape illustrated in FIG. 16) to respectively accommodate substantially circular and rectangular basins 12, 22 as described above. However, basin portions 56*a*, 56*b* may be of any shape to accommodate varying shaped thermal treatment system basins as described above. Reinforcing layer segment 58 is typically substantially elliptical and includes dimensions that encompass an area containing basin portions 56*a*, 56*b*. In other words, reinforcing layer segment 58 preferably extends across the drape to encompass and reinforce the areas extending slightly beyond and between basin portions 56*a*, 56*b*. As a result, when the drape is disposed over the thermal treatment system, the reinforcing layer segment extends partially onto the drape portions residing on cabinet top surface 32 adjacent and between basins 12, 22. Reinforcing layer segment 58 reinforces drape 17 by providing additional thickness to resist tearing and/or puncture stresses applied to the basin portions during normal use as described above. Reinforcing layer segment 58 may be of any shape that encompasses the basin portions and is typically bonded to the sterile surface of drape 17, however, the reinforcing layer segment may be bonded to either the sterile or non-sterile surface of the drape. The reinforcing layer segment edges may be bonded to the drape via material welds 52, or substantially the entire area of the reinforcing layer segment may be bonded to the drape to form a double laminate drape as described above. The primary drape layer may be of thinner construction as described above such that the cost of the drape is significantly reduced by selective reinforcement of stressed drape portions. Further, a single reinforcing layer segment or several reinforcing layer segments may be bonded to the drape, a large reinforcing area having a single or multiple layer segments may be constructed to encompass any drape portions receiving stress during normal use, or each reinforcing layer segment may be disposed integral with a corresponding primary drape layer portion in substantially the same manner described above to reinforce these portions and prevent tearing or puncturing of the drape. Moreover, additional reinforcing layers may be utilized on the drape wherein segments of the additional reinforcing layers are attached to the drape coincident existing reinforcing layer segments to further reinforce stressed drape portions in substantially the same manner described above.

It is to be understood that the multiple basin drapes described above may accommodate thermal treatment systems having any quantity of basins for congealing and/or heating a sterile medium wherein selected individual or large portions of the drape corresponding to the basins or other portions of the drape receiving stress during normal use may be reinforced in substantially the same manner described above. Alternatively, the multiple basin drape may be entirely reinforced by a reinforcing layer segment having substantially similar dimensions as the primary drape layer in substantially the same manner described above for the drape of FIG. 12. The reinforcing layer segment edges may be bonded to the drape, or substantially the entire area of the reinforcing layer segment may be bonded to the drape forming a double laminate drape as described above. Further, the primary drape layer and reinforcing layer segment may be constructed of thinner material, thereby substantially reducing drape costs since drapes including two bonded thinner layers are less expensive to produce than a single thicker layer drape.

Operation of thermal treatment systems with corresponding reinforced drapes is described with reference to FIGS. 8–17. Specifically, portions of drape 17 subjected to stress and wear, such as portions corresponding to the basin areas of the thermal treatment systems, the loadbearing corners of the cabinet top surfaces of the thermal treatment systems and areas on the top surface of the thermal treatment systems having buttons and switches, are identified based upon the particular drape application. Reinforcing layer segments 58 (FIGS. 8, 10, 12, 16), 58a–58b (FIG. 14), generally but not necessarily of the same type and thickness as the drape primary layer material, are positioned and bonded or attached to either the sterile or non-sterile surface of the appropriate drape coincident the identified drape portions to provide additional protection and tear resistance as described above. Each drape portion may be individually reinforced by a separate reinforcing layer segment corresponding to each drape portion (e.g., FIGS. 8, 10, 14), a larger reinforcing layer segment corresponding to several drape portions (e.g., FIG. 16), or a reinforcing layer segment corresponding to substantially the entire drape (e.g., FIG. 12) as described above. Further, additional reinforcing layers may be utilized on the drape wherein segments of the additional reinforcing layers are attached to the drape coincident existing reinforcing layer segments to further reinforce the drape as described above. Reinforcement of the drape enables the primary drape layer to be constructed of relatively thin drape material that, of itself, would not necessarily withstand the stress applied to the drape during normal use, but when reinforced by corresponding reinforcing layer segments 58, 58a–58b as described above, has sufficient strength to reliably prevent tearing and/or puncturing of the drape. The reinforced drape is subsequently disposed over the appropriate single or multiple basin thermal treatment system such that the reinforced drape portions coincide with areas of the thermal treatment system applying stress to the drape, and a drape receptacle is formed within each thermal treatment system basin as described above. The reinforcement drapes described above are especially suitable for use with thermal treatment systems generating surgical slush since these systems include drape manipulation and inherent localized stress. However, it is to be understood that the principles of the reinforced drapes equally apply to any thermal treatment systems warming and cooling surgical liquids that employ drapes as sterile containers disposed within thermal treatment system basins as described above.

An alternative manner in which to reinforce surgical drapes, while enabling immediate generation of sterile field during a surgical procedure and/or utilization of thinner and/or less expensive drapes is illustrated in FIG. 18. Initially, drape 17 is substantially similar to the drape described above for FIG. 1 and is positioned over a thermal treatment system of the type described above for FIG. 1 wherein a portion of the drape is pushed down into and conforms to basin 11 to form a drape receptacle for collecting congealed sterile medium. Drape 17 forms a sterile field above basin 11 to maintain sterility of the sterile medium and/or sterile slush. A reinforcing drape 45, similar to drape 17 and preferably an inexpensive basic non-fitted drape as described above, is disposed over drape 17 with a portion of reinforcing drape 45 disposed in the basin to form a drape receptacle in substantially the same manner described above for drape 17. Reinforcing drape 45 may be disposed over drape 17 either directly after placement of drape 17 on the thermal treatment system, or subsequent utilization or damage to the drape during a surgical procedure. The utilization of reinforcing drape 45 enables a sterile field to be immediately generated above basin 11 when underlying drape 17 tears or punctures during a surgical procedure without having to waste critical time disposing of the damaged drape. Alternatively, underlying and reinforcing drapes 17, 45 may each be of thinner construction, typically having a thickness comparable to the primary drape layer and reinforcement layer segments of the reinforced drapes described above. A thin reinforcing drape 45 is typically disposed over a thin underlying drape 17 in substantially the same manner described above directly after placement of the underlying drape on a thermal treatment system. A thin reinforcing drape 45 reinforces substantially the entire underlying drape to provide additional thickness to withstand stress applied to the drape during normal use as described above. The utilization of thin drapes reduces thermal treatment system costs, while enhancing drape malleability and handling in substantially the same manner described above.

Figure 19:
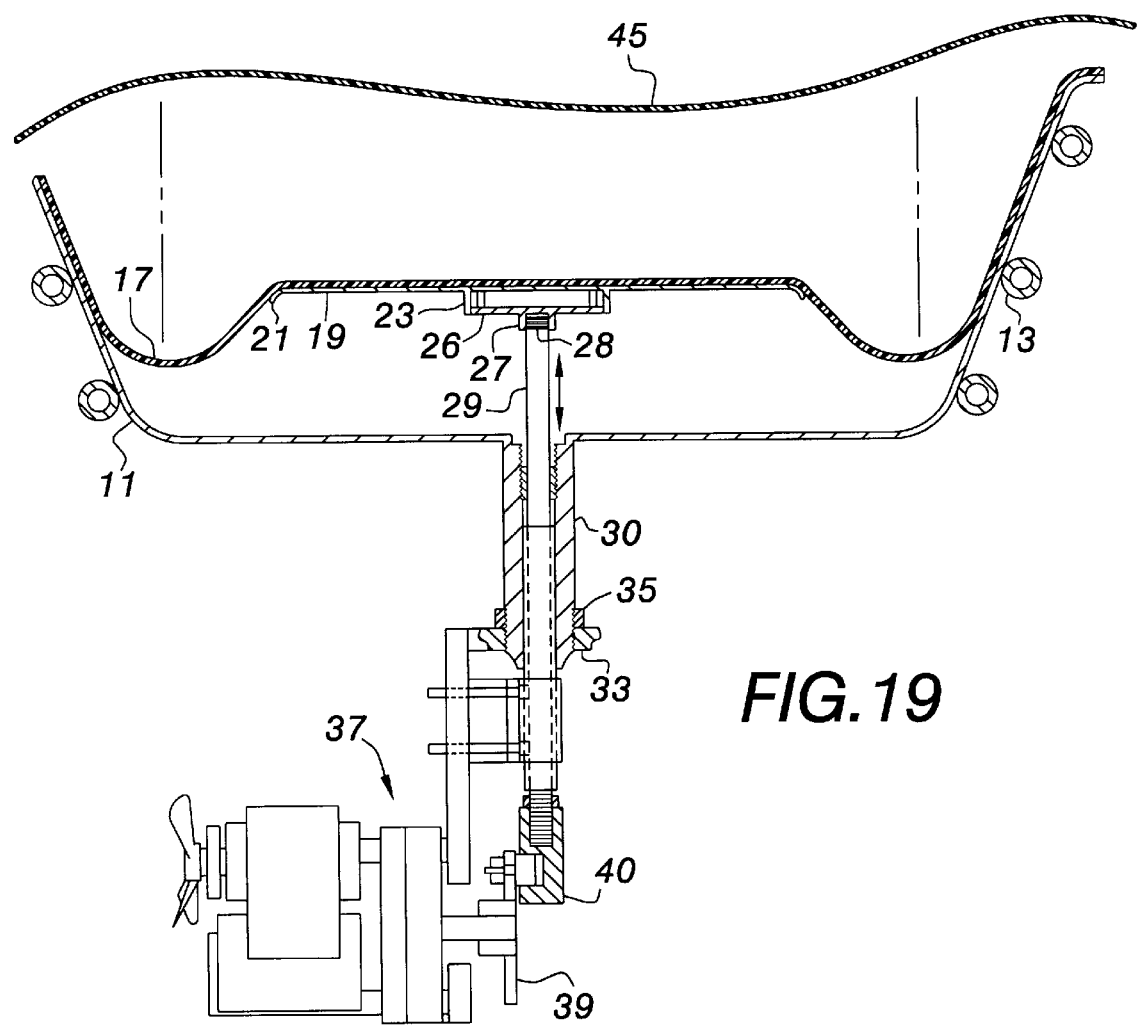
FIG. 19 is an exploded view in elevation and section of an additional reinforcing drape disposed over an underlying drape placed on a thermal treatment system having an automatic dislodgement mechanism according to yet another embodiment of the present invention.

The multiple drape embodiment further provides a cost effective manner in which to operate a thermal treatment system by enabling reuse of an underlying drape 17 as illustrated in FIG. 19. Initially, a drape 17, substantially similar to the underlying drapes described above, is positioned over a thermal treatment system having a dislodgement mechanism of the type described above for FIG. 3 to enable manipulation of drape 17 and dislodgement of congealed sterile medium. A portion of drape 17 is pushed down into and conforms to basin 11 to form a drape receptacle for collecting congealed sterile medium as described above. Specifically, drape 17 includes a plate 19 for engaging the dislodgement mechanism to enable manipulation of drape 17 and dislodgment of congealed sterile medium adhering to the drape as described above. A reinforcing drape 45, preferably an inexpensive basic non-fitted drape described above, is disposed over drape 17 with a portion of reinforcing drape 45 disposed in the basin to form a drape receptacle in substantially the same manner described above for drape 17. Reinforcing drape 45 may be disposed over drape 17 either directly after placement of drape 17 on the thermal treatment system, or subsequent utilization or damage to drape 17 during a surgical procedure. Generally, drapes including plate 19 tend to have increased costs because of the additional components and labor required to attach the plate to the drape. However, since reinforcing drape 45 provides a sterile field above drape 17, drape 17 may be reused for numerous surgical procedures, while reinforcing drape 45 may be implemented by an economical and inexpensive drape. Thus, economical or inexpensive reinforcing drape 45 is required to be replaced for each thermal treatment system use to provide a sterile field, while expensive specialized drape 17 having plate 19 is reused and purchased less frequently, thereby reducing overall drape and system costs.

This manner of drape reuse may also extend to drapes 17 including other specialized features, such as pre-formed portions, bladders for manipulating the drape, components for interfacing various dislodgement mechanisms to manipulate the drape or other features disclosed above in the aforementioned patents and copending applications. Drape and overall system costs are reduced as described above since the underlying expensive specialized drape is purchased less frequently than the economical overlying drape, thereby providing the sterile field required for each thermal treatment system use at reduced cost. For example, surgical drapes disclosed in the Faries, Jr. et al patent (5,524,643) include sensors for detecting leaks within a drape by detecting the presence of liquid (i.e., sterile medium). Since these drapes include electronic liquid detectors (i.e., sensors), the drapes tend to be rather expensive. However, an inexpensive reinforcing drape may be disposed over the sensor drape properly positioned on a thermal treatment system. If a leak occurs in the reinforcing drape, the underlying sensor drape detects the presence of liquid escaping the reinforcing drape and residing between the drapes in substantially the same manner described in the Faries Jr. et al (5,524,643) patent, thereby indicating the presence of a leak in the overlying reinforcing drape. Thus, the sensor drape operates in substantially the same manner when employed with a reinforcing drape. However, the sensor drape may be reused several times, while the inexpensive drape providing the sterile field is repurchased for each use, thereby reducing overall system costs by requiring purchase of the higher costing sensor drape less frequently.

Referring back to FIG. 19, the multiple drape embodiment may further be utilized with thermal treatment systems having dislodgement mechanisms wherein the multiple drape embodiment enhances manipulation of the drapes to dislodge congealed sterile medium adhered to the overlying reinforcing drape adjacent basin walls. In particular, co-pending U.S. Pat. application Ser. No. 08/810,104 recognizes that thermal treatment system dislodgement mechanisms employing a reciprocating up and down motion (e.g., the mechanism described in the Faries Jr. et al patent (U.S. Pat. No. 5,331,820) having a plate attached to the dislodgement mechanism, or the mechanism described above for FIGS. 3 and 19 having the plate attached to the drape) tend to draw drapes beneath the dislodgement mechanism reciprocating plate during thermal treatment system operation. This is typically accomplished by the reciprocating plate motion siphoning air from the area between a drape and the basin. When a drape is drawn under the mechanism in this fashion, the drape is not sufficiently manipulated, thereby inhibiting dislodgement of congealed sterile medium adhered to the drape adjacent basin walls. However, when a reinforcing drape 45 is disposed over an underlying drape 17 as described above, sufficient air flow exists between the drapes to prevent overlying reinforcing drape 45 from being drawn under reciprocating plate 19. In other words, the reciprocating plate motion can only siphon air residing between underlying drape 17 and basin 11 since underlying drape 17 functions as a barrier to prevent the reciprocating plate motion from siphoning air residing between the drapes. Although underlying drape 17 may be drawn under the dislodgement mechanism reciprocating plate, reinforcing drape 45 is still manipulated by the dislodgement mechanism to dislodge congealed sterile medium adhered to the reinforcing drape. Thus, reinforcing drape 45 is prevented from being drawn beneath reciprocating plate 19 and is manipulated by the dislodgement mechanism to dislodge congealed sterile medium adhered to that drape. Enhanced dislodgement may be accomplished in substantially the same manner described above for any other dislodgement mechanisms employing a reciprocating or other motion that may retard drape manipulation, such as the dislodgement mechanism disclosed in the aforementioned Faries, Jr. et al patent (U.S. Pat. No. 5,331,820).

Reinforcing drapes 45 may further be disposed over drapes placed on thermal treatment systems having other dislodgement mechanisms, warming a sterile medium (FIG. 4) or including multiple basins (FIG. 6) for warming and/or cooling a sterile medium in substantially the same manner described above. It is to be understood that any drape compatible with a thermal treatment system may be utilized as an underlying drape and that additional drapes 17 and/or 45 may be placed over each other in any fashion. Thus, thermal treatment systems may include multiple layers of drapes to quickly provide sterile fields above used or damaged drapes, to enable reuse of underlying drapes and to reduce system costs in substantially the same manner described above. Although the most cost effective approach is to utilize an inexpensive drape as reinforcing drape 45, any other drape compatible with a particular thermal treatment system may be utilized as a reinforcing drape. For example, a specialized drape (e.g., drape having sensors to detect leaks, or a drape having a bladder to dislodge congealed sterile medium) may be utilized as a reinforcing drape 45 for an underlying specialized drape 17 to provide a sterile field above the specialized drape and/or to combine specialized features to enhance thermal treatment system operation. Specialized drape features may be combined to enhance dislodgement of congealed sterile medium, for example, by utilizing a drape having a dislodgement feature, such as a bladder, as a reinforcement drape for a drape having a plate connected to a thermal treatment dislodgement mechanism. The combination of drape dislodgement features (e.g., the bladder and reciprocating plate) enhances dislodgement of congealed sterile medium by simultaneously employing plural dislodgement techniques. Thus, various combinations and quantities of reinforcing and underlying drapes may be utilized to reduce costs and/or enhance specific aspects of thermal treatment system operation.

It will be appreciated that the embodiments described above and illustrated in the drawings represent only a few of the many ways of implementing reinforced surgical drapes for use with thermal treatment systems.

The drapes (i.e., the primary drape layer and reinforcement layer segments) may include any material capable of collecting sterile medium (i.e., impervious to liquid) and maintaining sterility. Further, the reinforced and multiple drapes may be constructed to be utilized with thermal systems having any number of basins for warming, cooling and/or congealing liquid or other medium, and with any thermal treatment system dislodgement mechanisms, such as mechanisms twisting the drape, mechanisms including reciprocating plates, mechanisms for inflating and deflating bladders or any other mechanisms to manipulate the drape. The reciprocating plate may be bonded or attached to the drape by any conventional adhesives, and may be constructed of any suitably sturdy material. Similarly, the reinforcement layer segments may be bonded or attached to a drape by any known or conventional fastening techniques and/or adhesives wherein the reinforcement layer segments for a reinforcement layer may include any quantity of layer segments to reinforce a drape portion, may be of the same or different material and thickness as the primary drape layer, and may be of any size and cover any portion of the drape. Moreover, any quantity of additional reinforcing layers may be utilized on the drape wherein segments of the additional reinforcing layers are attached to either the sterile or non-sterile surfaces of the drape coincident existing reinforcing layer segments to further reinforce the drape (i.e., segments of the reinforcing layers may be stacked upon each other in any fashion and/or disposed on opposite surfaces of the drape such that the drape resides between the segments). The segments of the various reinforcing layers may vary in thickness such that the drape is reinforced by having thicker segments of a particular reinforcing layer or layers reinforce drape portions receiving higher amounts of stress. The multiple drapes may be placed on a thermal treatment system in any fashion to produce a sterile field, and any number of drapes may be arranged on the system such that the thermal treatment system may thermally treat and/or dislodge the congealed sterile medium through the drapes. The reinforced and multiple drapes may be of any thickness capable of containing a sterile medium, wherein a primary drape layer of a reinforced drape or each drape of the multiple drape embodiment may be typically of thinner construction than single layer drapes.

It is to be understood that the reinforced drape embodiment includes providing at least one additional reinforcing drape layer on any drape compatible with a thermal treatment system (e.g., drapes having preformed container portions, bladders, plates, sensors, etc. or any other features). Each reinforcing layer includes at least one segment wherein each segment may be of any size and is typically disposed on the drape coincident substantially the entire drape or at any specific location on the drape registering stress during use. Alternatively, the reinforcing layer segments may be disposed integral with the drape, thereby providing a drape having varying thickness. Further, the multiple drape embodiment includes placing any quantity of reinforcing drapes over a thermal treatment system (i.e., either heating, cooling or congealing a sterile medium) having a drape previously disposed thereon. The underlying drape may be any type of surgical drape compatible with the system, preferably being a more expensive drape performing other functions, such as enhancing dislodgement of congealed sterile medium. The reinforcing drape is preferably a more economical and inexpensive drape placed over the underlying (i.e., typically non-sterile) drape to provide a sterile field. This arrangement may be utilized for any surgical drapes compatible with a given thermal treatment system to enhance sterility via use of multiple drapes and enable reuse of the underlying drape to reduce overall system and drape costs. Thus, the underlying and more expensive drape is replaced less frequently than the economical drape which is replaced for each use.

From the foregoing description it will be appreciated that the invention makes available novel reinforced surgical drapes for use with thermal treatment systems wherein a single drape is selectively reinforced with additional drape layers, or multiple drapes are disposed over a thermal treatment system to produce a sterile field.

Having described preferred embodiments of new and improved reinforced surgical drapes for use with thermal treatment systems, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A surgical drape for use with a thermal treatment system having at least one basin disposed on a top surface of a system housing to thermally treat a sterile medium wherein said drape is disposed on the thermal treatment system such that said drape hangs down from the top surface and is disposed within each basin to form a drape receptacle within each basin to contain the sterile medium, said drape comprising:

a primary drape layer to provide a sterile field above each basin wherein said primary drape layer includes a plurality of portions with at least one of said primary drape layer portions being stressed during use of said drape on the thermal treatment system; and a secondary drape layer having at least one secondary drape layer segment wherein each said secondary drape layer segment is selectively disposed on a corresponding stressed portion of said primary drape layer to reinforce said primary drape layer such that said drape withstands stress to prevent damage to said drape and to maintain the sterile field above each basin.

2. The drape of claim 1 wherein each said secondary drape layer segment is disposed on a corresponding primary drape layer portion forming a drape receptacle within a basin.

3. The drape of claim 1 wherein a secondary drape layer segment is disposed on and encompasses a primary drape layer area including each primary drape layer portion forming a drape receptacle within a basin.

4. The drape of claim 1 wherein a secondary drape layer segment is disposed on and encompasses all of said primary drape layer.

5. The drape of claim 1 wherein each said secondary drape layer segment is disposed on a corresponding primary drape layer stressed portion such that edges of each said secondary drape layer segment are attached to said corresponding stressed portion of said primary drape layer.

6. The drape of claim 1 wherein each said secondary drape layer segment is disposed on a corresponding primary drape layer stressed portion such that all of each said secondary drape layer segment is attached to said corresponding stressed portion of said primary drape layer to form a double laminate drape.

7. The drape of claim 1 wherein said drape further includes at least one additional drape layer wherein each said additional drape layer has at least one drape layer segment, and wherein each said drape layer segment of each said additional drape layer is selectively disposed on said primary drape layer to reinforce said primary drape layer.

8. The drape of claim 1 wherein said secondary drape layer is integral with said primary drape layer.

9. A thermal treatment system for thermally treating a sterile medium comprising:

a system housing including a top surface;

a basin disposed on said top surface for containing the sterile medium;

thermal treatment means for thermally treating the sterile medium disposed in said basin;

a first drape having a first drape portion for hanging down from said top surface and for being disposed within said basin to form a drape receptacle; and a second drape disposed over said first drape having a second drape portion for hanging down from said top surface and for being disposed within said basin to form a second drape receptacle, wherein said second drape provides a sterile field above said basin to maintain sterility of the sterile medium.

10. The system of claim 9 further including:

a dislodgement mechanism for manipulating said first and second drape receptacles within said basin to dislodge congealed sterile medium adhered to said second drape receptacle adjacent basin walls.

11. The system of claim 10 wherein said first drape includes a plate that engages said dislodgement mechanism to manipulate said first and second drape receptacles.

12. The system of claim 9 further including at least one additional drape wherein each said additional drape is disposed on the thermal treatment system and within said basin over a previously disposed drape to form a drape receptacle within said basin, and wherein the most recently disposed drape provides a sterile field above said basin to maintain sterility of the sterile medium.

13. The system of claim 9 wherein said top surface includes a plurality of said basins, wherein said thermal treatment means thermally treats each said basin, wherein said first drape forms said first drape receptacle within each said basin, and wherein said second drape forms said second drape receptacle within each said basin and provides the sterile field above each said basin to maintain sterility of the sterile medium.

14. In a thermal treatment system having at least one basin disposed on a top surface of a system housing for thermally treating a sterile medium and a surgical drape hanging down from the top surface and being disposed within the basin to form a drape receptacle for containing the sterile medium, wherein said drape includes a primary drape layer to provide a sterile field above each basin and a secondary drape layer to reinforce said primary drape layer, and wherein said primary drape layer includes a plurality of portions with at least one portion being stressed during use on the thermal treatment system and said secondary drape layer includes at least one secondary drape layer segment, a method for maintaining the sterile field above each basin by preventing damage to said drape comprising the step of:

(a) selectively disposing each secondary drape layer segment on a corresponding stressed portion of said primary drape layer to reinforce said primary drape layer such that said drape withstands stress to prevent damage to said drape and to maintain the sterile field above each basin.

15. The method of claim 14 wherein step (a) further includes:

(a.1) disposing each secondary drape layer segment on a corresponding primary drape layer portion forming a drape receptacle within a basin.

16. The method of claim 14 wherein a first secondary drape layer segment is of sufficient size to encompass a plurality of said primary drape layer stressed portions, and step (a) further includes:

(a.1) disposing said first secondary drape layer segment on a primary drape layer area including each primary drape layer portion forming a drape receptacle within a basin.

17. The method of claim 14 wherein a first secondary drape layer segment is of sufficient size to encompass all of said primary drape layer, and step (a) further includes:

(a.1) disposing said first secondary drape layer segment on said primary drape layer.

18. The method of claim 14 wherein step (a) further includes:

(a.1) disposing each said secondary drape layer segment on a corresponding primary drape layer stressed portion by attaching edges of each said secondary drape layer segment to said corresponding stressed portion of each said primary drape layer.

19. The method of claim 14 wherein step (a) further includes:

(a.1) disposing each said secondary drape layer segment on a corresponding primary drape layer stressed portion by attaching all of each said secondary drape layer segment to said corresponding stressed portion of said primary drape layer to form a double laminate drape.

20. The method of claim 14 wherein said drape further includes at least one additional drape layer wherein each said additional drape layer has at least one drape layer segment and step (a) further includes:

(a.1) selectively disposing each drape layer segment of each additional drape layer on said primary drape layer to reinforce said primary drape layer.

21. The method of claim 14 wherein step (a) further includes:

(a.1) disposing each said secondary drape layer segment integral with said primary drape layer.

22. A method for maintaining a sterile field within a thermal treatment system having at least one basin disposed on a top surface of a system housing to thermally treat a sterile medium and a surgical drape hanging down from the top surface and disposed within each basin to form a drape receptacle within each basin to contain the sterile medium, said method comprising the steps of:

(a) forming said drape having a primary drape layer to provide the sterile field above each basin and a secondary drape layer having at least one secondary drape layer segment wherein said primary drape layer includes a plurality of portions with at least one of said primary drape layer portions being stressed during use of said drape on the thermal treatment system, and (b) selectively disposing each secondary drape layer segment on a corresponding stressed portion of said primary drape layer to reinforce said primary drape layer such that said drape withstands stress to prevent damage to said drape and maintain the sterile field above each basin.

23. The method of claim 22 wherein step (a) further includes:

(a.1) forming said drape to include at least one additional drape layer wherein each additional drape layer has at least one drape layer segment; and step (b) further includes:

(b.1) disposing each drape layer segment of each additional drape layer on said primary drape layer to reinforce said primary drape layer.

24. The method of claim 22 wherein step (b) further includes:

(b.1) disposing each said secondary drape layer segment such that each said secondary drape layer segment is integral with said primary drape layer.

25. In a thermal treatment system having a basin disposed on a top surface of a system housing for thermally treating a sterile medium, a method for maintaining a sterile field above the basin comprising the steps of:

(a) disposing a first drape on the thermal treatment system such that a first drape portion hangs down from said top surface and is disposed with the basin to form a first drape receptacle;

(b) disposing a second drape over said first drape such that a second drape portion hangs down from said top surface and is disposed within said basin to form a second drape receptacle wherein the second drape provides the sterile field above the basin to maintain sterility of the sterile medium; and (c) thermally treating the sterile medium disposed within said second drape receptacle in the basin.

26. The method of claim 25 wherein the thermal treatment system further includes a dislodgement mechanism, and said method further includes the step of:

(d) manipulating said first and second drape receptacles within the basin via the dislodgement mechanism to dislodge congealed sterile medium adhered to said second drape receptacle adjacent basin walls.

27. The method of claim 26 wherein said first drape includes a plate and step (d) further includes:

(d.1) engaging said dislodgement mechanism with the plate to manipulate said first and second drape receptacles.

28. The method of claim 25 wherein step (b) further includes:

(b.1) disposing at least one additional drape over the thermal treatment system wherein each said additional drape is disposed over a previously disposed drape and forms a drape receptacle within the basin, and wherein the most recently disposed drape provides a sterile field above the basin to maintain sterility of the sterile medium.

29. The method of claim 25 wherein the thermal treatment system includes a plurality of basins disposed on the top surface, and step (a) further includes:

(a.1) disposing said first drape within each said basin to form said first drape receptacle within each basin;

step (b) further includes:

(b.1) disposing said second drape within each said basin to form said second drape receptacle within each said basin and to provide the sterile field above each basin; and step (c) further includes:

(c.1) thermally treating the sterile medium disposed in each basin.

30. In a thermal treatment system having at least one basin disposed on a top surface of a system housing for thermally treating a sterile medium and a surgical drape hanging down from the top surface and being disposed within each basin to form a drape receptacle within each basin to contain the sterile medium, a method for ensuring the presence of a sterile field above each basin comprising the step of:

(a) placing a second drape over said surgical drape wherein said second drape ensures the presence of the sterile field above each basin by providing a sterile field above said surgical drape.

31. The method of claim 30 wherein step (a) further includes:

(a.1) placing at least one additional drape over a previously disposed drape wherein the most recently disposed drape ensures the presence of the sterile field above each basin by providing a sterile field above each said additional drape and said previously disposed drape.

32. The method of claim 30 wherein said surgical drape is subject to damage during use on the thermal treatment system, and step (a) further includes:

(a.1) placing said second drape over said surgical drape wherein said second drape ensures the presence of the sterile field above each basin by providing a sterile field above said surgical drape incurring damage during use of said surgical drape on the thermal treatment system.

33. The method of claim 30 wherein said surgical drape is non-sterile, and step (a) further includes:

(a.1) placing said second drape over said non-sterile surgical drape wherein said second drape ensures the presence of the sterile field above each basin by providing a sterile field above said non-sterile surgical drape.

34. The method of claim 30 wherein the thermal treatment system includes a dislodgement mechanism and said surgical drape includes a plate that engages said dislodgement mechanism to manipulate said surgical drape, and step (a) further includes:

(a.1) placing said second drape over said surgical drape such that the dislodgement mechanism manipulates said surgical drape and said second drape.

* * * * *